United States Patent [19]

Warriner

[11] Patent Number: Plant 6,911

[45] Date of Patent: Jul. 11, 1989

[54] ROSE PLANT JACWHIF

[75] Inventor: William A. Warriner, Tustin, Calif.

[73] Assignee: Jackson & Perkins Company, Medford, Oreg.

[21] Appl. No.: 126,875

[22] Filed: Nov. 30, 1987

[51] Int. Cl.[4] ..... A01H 5/00

[52] U.S. Cl. ..... Plt./23

[58] Field of Search ..... Plt./12, 23

*Primary Examiner*—Robert E. Bagwill

*Attorney, Agent, or Firm*—Majestic, Parsons, Siebert & Hsue

[57] ABSTRACT

A rose variety of the floribunda class is provided having an extremely long vase life for the buds and flowers, short to medium length cutting stems (less than twenty inches), high resistance to powdery mildew, and excellent flower production of long-lasting, white flowers having a golden, or orangish, cast.

1 Drawing Sheet

SUMMARY OF THE DISCOVERY

The present discovery relates to a new and distinct variety of rose plant of the floribunda class, which I discovered in a cultivated area and I asexually reproduced. This new rose variety is a mutation of the rose plant designated "Kortexung" described and illustrated in pending U.S. Plant patent application Ser. No. 27,619, filed Oct. 26, 1987, inventor Kordes, incorporated herein by reference and of common assignment herewith.

The rose plant of the present discovery has a unique combination of characteristics which are outstanding in the new variety and which distinguish it from the rose plant Kortexung as well as form all other varieties of which I am aware. For example, this new rose variety has: White buds and flowers with a golden or orangish cast, rather than the light pink buds of the Kortexung variety.

Asexual reproduction of this new variety by budding, as performed at Wasco, Calif., shows that the foregoing characteristic and distinction comes true to form and is established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE DISCOVERY

The following is a detailed description of my new rose variety, which has been denominated "Jacwhif". Color terminology is in accordance with the Royal Horticultural Society Colour Chart except where an ordinary dictionary significance for the color is apparent.

Discovery of this mutation was in a cultivated area (a nursery) in Irvine, Calif., and observations of the buds and flowers of the asexually reproduced plant were made in a nursery at Irvine, Calif. Except as specifically indicated, the new rose variety is identical to the Kortexung variety.

Flower

The blooming habit is recurrent and continuous. The bud size is one to one and one-half inches when the petals start to unfurl. The bud form is long, pointed ovoid. By contrast to the Kortexung variety, the bud color when sepals first divide is near Orange Group 27D; when half blown the upper side of petals is near Orange Group 27D, and the lower side of petals is near Orange Group 27D. The sepals have a color near Green Group 138B. The surface texture is smooth with some very fine hairs. There are three appendaged sepals lightly appendaged, and two unappendaged sepals with hairy edge. The receptacle color is near Green Group 138B of a funnel shape, small size and smooth surface. The peduncle is of medium length, smooth surface with some very fine hairs. Peduncle color is medium green, and the peduncle is stiff and erect.

Bloom

Bloom size is small, with an average open size of two and one-half to three inches, and borne singly when grown in a greenhouse. When grown in a garden, then disbudding is required because a flowering shoot branches into three to five stems with blossoms; however, when grown in a greenhouse this occurs very rarely so very little disbudding is required. The stems are strong, and medium to short. The form when first open is high center. This form is retained to the end. The outer petals curl back quill fashion. Under normal conditions there are thirty petals. Unlike the Kortexung variety, the upper side of petal at the flower center is near Orange Group 27D, as is the reverse side of the petals, and the base of petals has a white semicircle near White Group 155B with the major color being near Orange Group 27D. There are no variegations. The general tonality at the end of the first day shows no change in color. At the end of the third day, there remains no discoloration.

The fragrance is slight. The petal texture is thick, of a deltoid shape and the tips are slightly recurved and becoming quilled.

The arrangement is imbricated with no petaloids in the center. The blooms drop off cleanly, and last both on the plant and as a cut flower for a very long time.

Reproductive Parts

The anthers are medium size, of yellow color and arranged regularly around the styles. The pollen is pale yellow, and the styles and stigmas are white.

Plant

A very vigorous growth of bush form.

Foliage

Medium size, sparse in quantity. The new foliage is reddish, and the old foliage is dark green near Green Group 139A. Normal mid-stem leaves have five to seven leaflets.

The leaflets are of an oval pointed shape, are glossy, and have a smooth texture with a serrated edge. The serration is single and medium in size. Petiole rachis is green and petiole underside is smooth with few prickles. Stipules are short and bearded. The foliage is resistant to mildew under normal growing conditions at Irvine, Calif.

Wood

New wood is light green, with a smooth bark. Old wood is green with a smooth bark.

Prickles

There are few prickles on main canes from the base and few on laterals from the main canes. The form is medium and straight. Color when young is red.

Small Prickles

There are no small prickles on the main stalks or on the laterals.

Parentage

A color mutation of the Kortexung variety.

Classification

Botanical is rosa hybrid. Commercial is floribunda.

I claim:

1. A new and distinct variety of rose plant and parts thereof of the floribunda class substantially as herein shown and described, characterized particularly as to novelty by the unique combination of its extremely long vase life, short to medium length cutting stems, high resistance to powdery mildew, excellent flower production, and long-lasting white color with a golden, or orangish, cast.

* * * * *

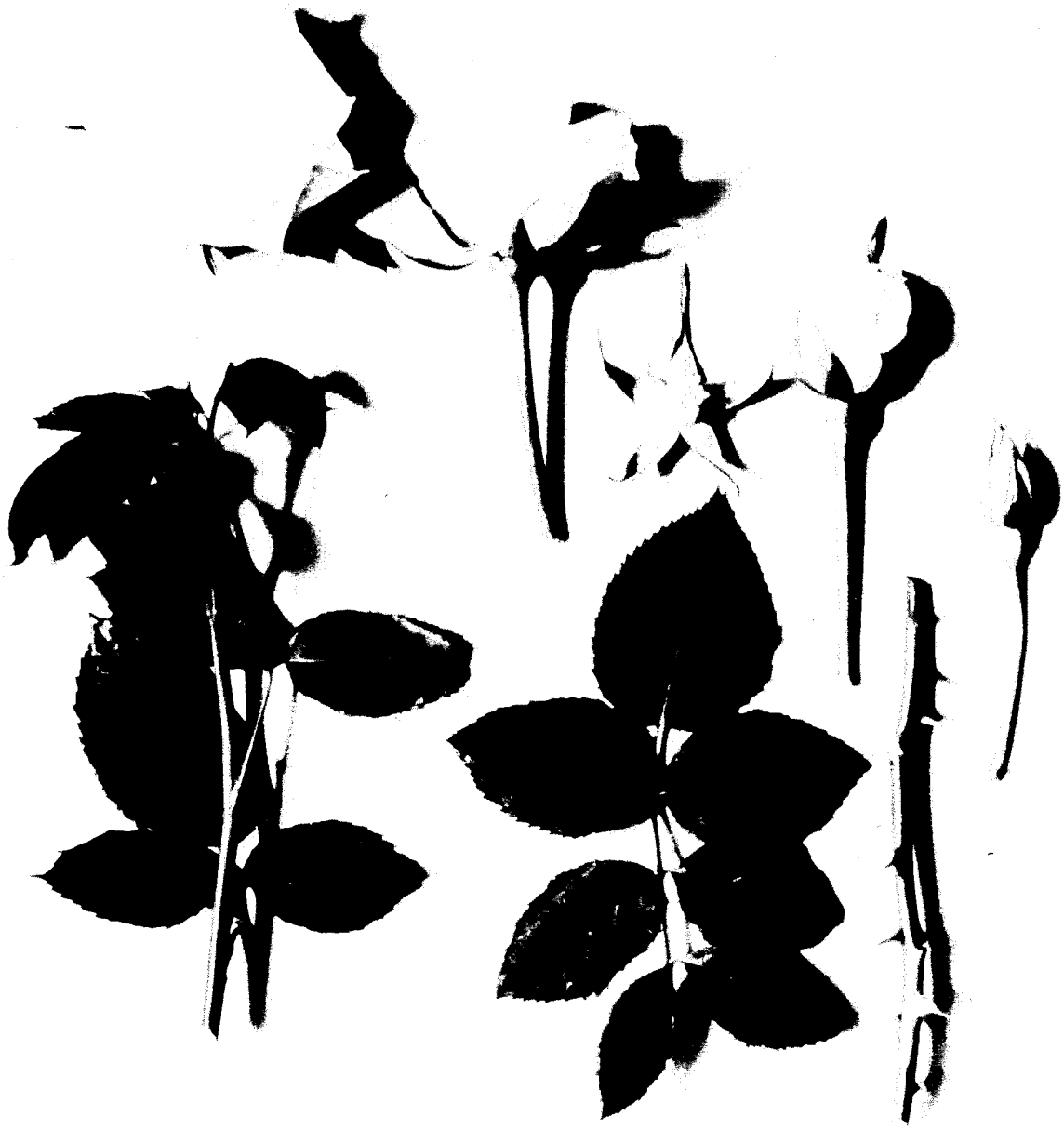
Jacwhif